United States Patent
Govindarajan et al.

(10) Patent No.: US 10,662,129 B2
(45) Date of Patent: May 26, 2020

(54) METHODS FOR PRODUCING PROPYLENE BY THE DEHYDROGENATION OF PROPANE

(71) Applicant: SABIC Global Technologies B.V., Bergen op Zoom (NL)

(72) Inventors: Deepa Govindarajan, Bangalore (IN); Venkatesan Chithravel, Bangalore (IN); B. V. Venugopal, Bangalore (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/063,026

(22) PCT Filed: Jan. 12, 2017

(86) PCT No.: PCT/IB2017/050160
§ 371 (c)(1),
(2) Date: Jun. 15, 2018

(87) PCT Pub. No.: WO2017/125836
PCT Pub. Date: Jul. 27, 2017

(65) Prior Publication Data
US 2018/0370873 A1 Dec. 27, 2018

Related U.S. Application Data

(60) Provisional application No. 62/281,370, filed on Jan. 21, 2016.

(51) Int. Cl.
*C07C 5/48* (2006.01)
*B01J 38/18* (2006.01)
(Continued)

(52) U.S. Cl.
CPC ............... *C07C 5/48* (2013.01); *B01J 21/04* (2013.01); *B01J 23/42* (2013.01); *B01J 23/96* (2013.01);
(Continued)

(58) Field of Classification Search
None
See application file for complete search history.

(56) References Cited

U.S. PATENT DOCUMENTS

| 2,773,014 A | 12/1956 | Snuggs et al. | 208/65 |
| 4,902,849 A * | 2/1990 | McKay | B01J 23/005 585/660 |

(Continued)

FOREIGN PATENT DOCUMENTS

WO WO2013009820 A1 1/2013

OTHER PUBLICATIONS

Dong et al. "Effects of Steam on the Structure of Pt—Sn/ZnAl$_2$O$_4$ Catalysts." Acta Physico-Chimica Sinica, 15:4 (1999) 289-292.
(Continued)

*Primary Examiner* — Ali Z Fadhel
(74) *Attorney, Agent, or Firm* — Norton Rose Fulbright US LLP

(57) ABSTRACT

Methods for producing propylene by the dehydrogenation of propane are provided. Methods can include introducing a first gas mixture including propane to a dehydrogenation catalyst at a temperature of at least about 570° C., introducing a second gas mixture including steam and air to the dehydrogenation catalyst at a temperature of at least about 550° C., and allowing the second gas mixture to subsist therewith for at least about one hour. Methods can further include introducing a third gas mixture including hydrogen to the dehydrogenation catalyst at a temperature of at least about 500° C.

19 Claims, 2 Drawing Sheets

(51) Int. Cl.
  *B01J 23/96* (2006.01)
  *B01J 21/04* (2006.01)
  *B01J 23/42* (2006.01)
  *B01J 38/12* (2006.01)
  *B01J 38/02* (2006.01)
  *B01J 38/06* (2006.01)
  *B01J 38/10* (2006.01)
  *C07C 11/06* (2006.01)

(52) U.S. Cl.
  CPC .............. *B01J 38/02* (2013.01); *B01J 38/06* (2013.01); *B01J 38/10* (2013.01); *B01J 38/12* (2013.01); *B01J 38/18* (2013.01); *C07C 11/06* (2013.01); *C07C 2523/42* (2013.01); *Y02P 20/52* (2015.11); *Y02P 20/584* (2015.11)

(56) References Cited

U.S. PATENT DOCUMENTS

| | | | |
|---|---|---|---|
| 5,087,792 A | 2/1992 | Cottrell et al. | 585/661 |
| 6,916,756 B2 | 7/2005 | Schindler et al. | 502/38 |
| 2004/0029715 A1 | 2/2004 | Schindler et al. | 502/50 |
| 2012/0157737 A1* | 6/2012 | Olbert | B01J 8/0484 585/440 |
| 2014/0200385 A1 | 7/2014 | Pretz et al. | 585/660 |
| 2016/0272559 A1* | 9/2016 | Pretz | C07C 5/3337 |

OTHER PUBLICATIONS

International Search Report and Written Opinion from PCT/IB2017/050160, dated Apr. 20, 2017, 9 pages.

Kogan et al. "Dehydrogenation of propane on modified Pt/θ-alumina and Performance in hydrogen and steam environment." Applied Catalysts A: General 208 (2001) 185-191.

Ruckenstein et al. "Redispersion of Platinum Crystallites Supported on Alumina—Role of Wetting." J. Catalysis, 59:1 (1979) 109-122.

Ruckenstein et al. "The Effect of Steam on Supported Metal Catalysts." J. Catalysis, 100:1 (1986) 1-16.

Schaper et al. "The influence of high partial steam pressures on the sintering of lanthanum oxide doped gamma alumina." Applied Catalysis, 9:1 (1984) 129-132.

Schlaffer et al. "Aging of silica-alumina cracking catalyst. I. Kinetics of Structural Changes by Heat and Steam." J. Phys. Chem., 61:6 (1957) 714-722.

Sushumna et al. "Redispersion of Pt/Alumina via Film Formation." J. Catalysis, 108:1 (1987) 77-96.

Vora. "Development of Dehydrogenation Catalysts and Processes." Topics in Catalysis, 55:19 (2012) 1297-1308.

Caspary et al., "Dehydrogenation of alkanes," Handbook of Heterogeneous Catalysis (Weinheim 2008, Wiley-VCH), Section 14.6, 33 pages.

* cited by examiner

METHODS FOR PRODUCING PROPYLENE BY THE DEHYDROGENATION OF PROPANE

CROSS-REFERENCE TO RELATED APPLICATIONS

This application is a national phase application under 35 U.S.C. § 371 of International Application No. PCT/IB2017/050160 filed Jan. 12, 2017, which claims priority to U.S. Provisional Patent Application No. 62/281,370 filed Jan. 21, 2016. The entire contents of each of the above-referenced disclosures is specifically incorporated by reference herein without disclaimer.

FIELD

The disclosed subject matter relates to methods for producing propylene by the dehydrogenation of propane.

BACKGROUND

Propylene can be an important feedstock for a variety of chemical processes. For example, propylene can be used in the production of polypropylene, propylene oxide, acrylonitrile, cumene, butyraldehyde, and acrylic acid. Propylene can be produced as a by-product of certain petrochemical processes, including the steam cracking, e.g., of ethane, liquefied petroleum gas (LPG), and/or naphtha and fluid catalytic cracking.

Certain methods for producing propylene are known in the art, including by olefins metathesis, methanol-to-olefins via syngas, high severity fluid catalytic cracking, and propane dehydrogenation. For example, propane dehydrogenation can be used to convert propane to propylene using a dehydrogenation catalyst. However, the dehydrogenation reaction can have side reactions, leading to catalyst deactivation.

Certain methods for regenerating dehydrogenation catalysts are known in the art. For example, U.S. Pat. No. 6,916,756 discloses a method of regenerating a dehydrogenation catalyst, including flushing the catalyst with an inert gas and passing an oxygen-containing gas mixture including an inert gas through the catalyst while increasing the oxygen concentration. U.S. Patent Publication No. 2014/0200385 discloses a process of regenerating a partially deactivated dehydrogenation catalyst. The method includes heating the catalyst to a temperature of at least 660° C., conditioning the heated catalyst in an oxygen-containing atmosphere and, optionally, stripping molecular oxygen from the conditioned catalyst.

However, there remains a need for improved techniques for the dehydrogenation of propane, including improved techniques for regenerating dehydrogenation catalysts.

SUMMARY OF THE DISCLOSED SUBJECT MATTER

The disclosed subject matter provides methods for producing propylene by the dehydrogenation of propane.

In certain embodiments, an exemplary method for producing propylene includes introducing a first gas mixture including propane to a dehydrogenation catalyst at a temperature of at least about 570° C., introducing a second gas mixture including steam and air to the dehydrogenation catalyst at a temperature of at least about 550° C., and allowing the second gas mixture to subsist therewith for at least about one hour. The method can further include introducing a third gas mixture including hydrogen to the dehydrogenation catalyst at a temperature of at least about 500° C.

In certain embodiments, the first gas mixture can include steam. For example, the first gas mixture can include steam and propane in a molar ratio from about 2 mol/mol to about 4 mol/mol. The dehydrogenation catalyst can include platinum. The platinum can be supported on alumina.

In certain embodiments, the second gas mixture subsists with the dehydrogenation catalyst for from about one hour to about four hours. The air in the second gas mixture can include oxygen, such that the second gas mixture includes from about 2 mol-% to about 10 mol-% oxygen. The second gas mixture can include steam and air in a molar ratio from about 1 mol/mol to about 12 mol/mol.

In certain embodiments, from about 35 mol-% to about 50 mol-% of the propane in the first gas mixture can be converted. In particular embodiments, about 45 mol-% of the propane in the first gas mixture is converted. The propane can be reacted in the presence of the dehydrogenation catalyst at a temperature of about 550° C. to about 630° C. to generate a product gas mixture including propylene. In certain embodiments, the temperature can be about 630° C. The reaction can be performed in a first reactor. The reaction can have a propylene selectivity of greater than about 86%.

In certain embodiments, the method further includes transferring the dehydrogenation catalyst to a second reactor including the second gas mixture after the reaction. The dehydrogenation catalyst can be regenerated in the second reactor at a temperature from about 550° C. to about 600° C. In certain embodiments, the third gas mixture can be introduced to the dehydrogenation catalyst in the second reactor. In certain other embodiments, the dehydrogenation catalyst can be transferred to a third reactor including the third gas mixture after it is regenerated.

DETAILED DESCRIPTION

The presently disclosed subject matter provides methods for producing propylene. In certain embodiments, the disclosed subject matter provides methods for the dehydrogenation of propane to form propylene.

Figure 1:
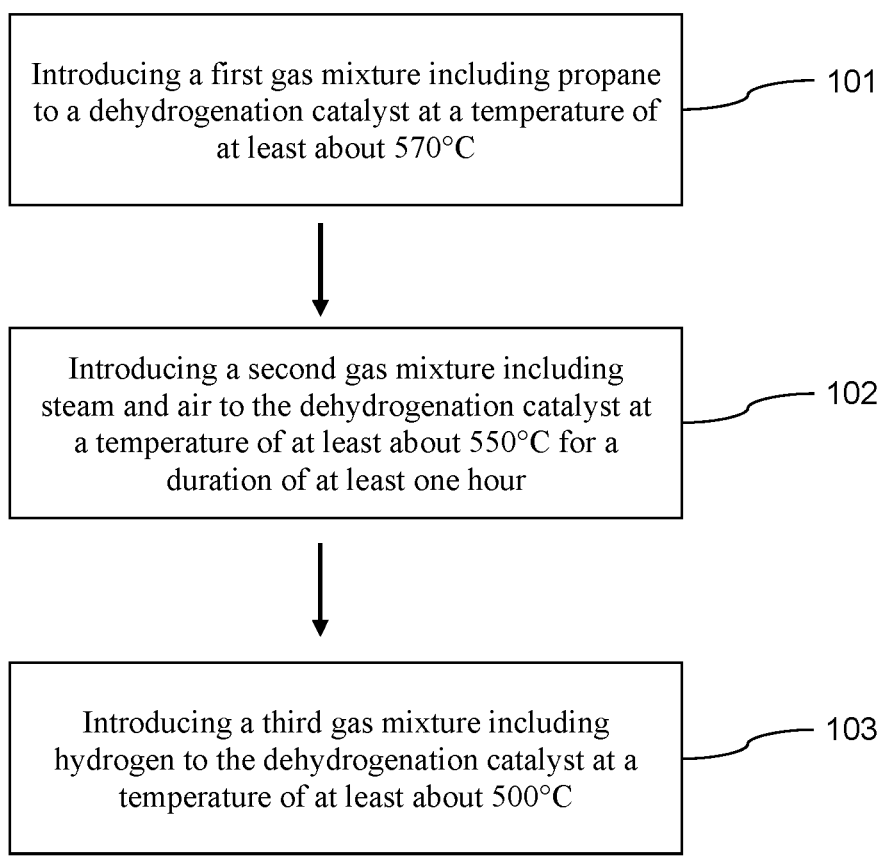
FIG. 1 depicts a method for producing propylene according to one exemplary embodiment of the disclosed subject matter.

For the purpose of illustration and not limitation, FIG. 1 is a schematic representation of a method according to a non-limiting embodiment of the disclosed subject matter. The method 100 can include introducing a first gas mixture 101 including propane to a dehydrogenation catalyst at a temperature of at least about 570° C.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

In certain embodiments, the propane in the first gas mixture can be diluted with another gas, e.g., steam, carbon dioxide, methanol, air, and/or hydrogen. For example, the propane in the first gas mixture can be diluted with steam. Use of steam as a diluent can provide certain advantages, including increasing the temperature of the first gas mixture, increasing the dehydrogenation reaction rate and propane conversion, and reducing coke (i.e., carbonaceous deposits) formation on the dehydrogenation catalyst. The first gas mixture can include steam and propane in a particular molar ratio. For example, the molar ratio of steam to propane in the first gas mixture can be from about 2 mol/mol to about 4 mol/mol. In particular embodiments, the molar ratio of steam to propane in the first gas mixture is about 4 mol/mol.

In certain embodiments, the dehydrogenation catalyst can include platinum (Pt). The platinum can be supported on an inert material. For example, the platinum can be supported on an alumina ($Al_2O_3$) support. In certain embodiments, the support can further include zinc oxide (ZnO) and/or calcium oxide (CaO). In certain embodiments, the dehydrogenation catalyst can further include one or more promoters, i.e., metals, such as Tin (Sn), Gallium (Ga), and/or Indium (In).

The first gas mixture can be introduced to the dehydrogenation catalyst in a first reactor. The reactor can be of any suitable type for the dehydrogenation of propane. By way of example, and not limitation, such reactors include tubular reactors, such as fixed bed tubular reactors and fluidized bed tubular reactors, moving bed reactors, and panel reactors. For example, and not limitation, suitable reactors are provided in European Patent No. EP2173470, the contents of which are hereby incorporated by reference in its entirety.

In certain embodiments, the first gas mixture can undergo a dehydrogenation reaction. For example, the dehydrogenation of propane ($C_3H_8$) to form propylene ($C_3H_6$) can be represented by Formula 1:

$$C_3H_8 \leftrightarrows C_3H_6 + H_2 \quad \text{(Formula 1)}$$

The dehydrogenation of propane is equilibrium driven and endothermic. Therefore, it can be desirable to conduct the reaction at high temperatures, e.g., greater than about 570° C. In certain embodiments, the reaction temperature can be from about 500° C. to about 700° C., from about 550° C. to about 650° C., or from about 570° C. to about 630° C. In particular embodiments, the reaction temperature is about 630° C. By way of example, and not limitation, the pressure of the dehydrogenation reaction can be less than about 5 barg, less than about 2 barg, or less than about 1.5 barg.

In certain embodiments, the dehydrogenation reaction produces a product gas mixture. The product gas mixture can include propylene, as well as unconverted propane and/or diluent, if any, from the first gas mixture. In certain embodiments, from about 15 mol-% to about 70 mol-%, from about 25 mol-% to about 60 mol-%, or from about 35 mol-% to about 50 mol-% of the propane in the first gas mixture is converted. The dehydrogenation reaction can have a propylene selectivity of greater than about 75%, greater than about 80%, or greater than about 86%. In certain embodiments, propylene selectivity can be greater than about 89%. The product mixture can also include reaction products from side reactions. For example, in certain embodiments, the product mixture can include methane, ethane, ethylene, carbon monoxide, and/or carbon dioxide.

The dehydrogenation reaction can have certain side reactions that can form coke and/or high molecular weight byproducts. These byproducts can accumulate on the surfaces and in the pores of the dehydrogenation catalyst and reduce catalyst activity. Therefore, in certain embodiments, the method can further include regenerating the dehydrogenation catalyst. For example, and with reference to FIG. 1, the method 100 can include introducing a second gas mixture 102 including steam and air to the dehydrogenation catalyst at a temperature of at least about 550° C. for a duration of at least one hour.

The second gas mixture can include steam and air in a certain molar ratio. For example, the molar ratio of steam to air in the second gas mixture can be from about 1 mol/mol to about 12 mol/mol. The air in the second gas mixture can include oxygen gas ($O_2$), such that the amount of oxygen gas in the second gas mixture can be from about 2 mol-% to about 12 mol-%, or from about 4 mol-% to about 8 mol-%.

In certain embodiments, the dehydrogenation catalyst is regenerated in the presence of the second gas mixture when its activity has declined by a certain percentage (e.g., as measured by propane conversion). For example, in certain embodiments, the method can include regenerating the dehydrogenation catalyst when propane conversion has declined by about 10%, about 20%, about 30%, or about 40%, or about 50% as compared to propane conversion using a fresh catalyst. In certain embodiments, the method can include regenerating the dehydrogenation catalyst when the catalyst is completely deactivated.

In certain embodiments, the dehydrogenation catalyst can be transferred from a first reactor, i.e., where the dehydrogenation reaction takes place, to a second reactor for catalyst regeneration. The reactor for catalyst regeneration can be operated batch-wise or continuously. For example, the reactor for catalyst regeneration can be a batch reactor or a tubular reactor.

In certain embodiments, the dehydrogenation catalyst is contacted with the second gas mixture for a particular duration of time. For example, regeneration catalyst can be contacted with the second gas mixture for at least about one hour. In certain embodiments, the dehydrogenation catalyst is contacted with the second gas mixture for from about one hour to about four hours. In certain embodiments, the dehydrogenation catalyst can be contacted with the second gas mixture at a temperature from about 550° C. to about 600° C. and a pressure from about 0.5 barg to about 4 barg.

The dehydrogenation catalyst can be further reduced to regenerate its activity. For example, the method 100 can further include introducing a third gas mixture 103 including hydrogen to the dehydrogenation catalyst at a temperature of at least about 500° C. In certain embodiments, the third gas mixture is a hydrogen stream, e.g, containing greater than about 85 vol-%, greater than about 90 vol-%, greater than about 95 vol-%, greater than about 97 vol-%, or greater than about 99 vol-% hydrogen.

In certain embodiments, the third gas mixture can be introduced to the dehydrogenation catalyst in the second reactor, i.e., the same reactor as the second gas mixture. Thus, in such embodiments, catalyst regeneration and reduction can occur in the same reactor, and only two reactors are required. In other certain embodiments, the dehydrogenation catalyst can be transferred from the second reactor to a third reactor prior to being reduced by the third gas mixture. The reactor for catalyst reduction can be operated batch-wise or continuously. For example, the reactor for catalyst reduction can be a batch reactor or a tubular reactor.

The methods of the presently disclosed can provide advantages over certain existing technologies. An exemplary advantage includes increasing catalyst lifetime by repeatedly regenerating deactivated catalyst to restore dehydrogenation catalyst activity. For example, the dehydrogenation catalyst activity can be completely restored to the level of a fresh catalyst. In certain embodiments, catalyst activity can be improved compared to fresh catalyst. The examples below illustrate these and other advantages.

The following examples provide methods for the dehydrogenation of propane to form propylene in accordance with the disclosed subject matter. However, the following examples are merely illustrative of the presently disclosed subject matter and should not be considered as a limitation in any way.

Example 1: Propane Dehydrogenation with Fresh Catalyst

In this Example, about 10 g of a fresh platinum catalyst was loaded into a reactor, dried, and reduced with hydrogen gas at a flow rate of 100 ml/min for thirty minutes. A feed stream containing steam and propane in a ratio of 4 mol/mol was fed to the reactor. The reaction had a temperature of 570° C., a pressure of 22 psig, and a liquid hourly space velocity (LHSV) of 2.5 $h^{-1}$. Propane conversion was 35% and propylene selectivity was 86%.

Example 2: Propane Dehydrogenation after Catalyst Regeneration for 1 Hour

After conducting Example 1, the same catalyst was regenerated with a mixture of air and steam at 550° C. for 1 hour. The flow rate of air was varied from 50 ml/min to 100 ml/min, while the flow rate of steam was held constant at 0.3215 ml/min. The catalyst was then reduced with hydrogen gas at a flow rate of 100 ml/min for thirty minutes. A feed stream containing steam and propane in a ratio of 4 mol/mol was fed to the reactor. The reaction had a temperature of 570° C., a pressure of 22 psig, and a liquid hourly space velocity (LHSV) of 2.5 $h^{-1}$. Propane conversion was 39% and propylene selectivity was 88%.

Example 3: Propane Dehydrogenation after Catalyst Regeneration for 4 Hours

After conducting Examples 2 and 3, the same catalyst was regenerated with a mixture of air and steam at 550° C. for 1 hour. The flow rate of air was 75 ml/min and the flow rate of steam was 0.3215 ml/min. The catalyst was then reduced with hydrogen gas at a flow rate of 100 ml/min for thirty minutes. A feed stream containing steam and propane in a ratio of 4 mol/mol was fed to the reactor. The reaction had a temperature of 570° C., a pressure of 22 psig, and a liquid hourly space velocity (LHSV) of 2.5 $h^{-1}$. Propane conversion was 45% and propylene selectivity was 89.6%. Table 1 compares the results of Examples 1-3.

TABLE 1

Propane Conversion and Product Selectivity of Examples 1-3

| Example | Propane Conversion (mol-%) | Product Selectivity (dry C mol-%) | | | | | | |
| --- | --- | --- | --- | --- | --- | --- | --- | --- |
| | | $C_3H_6$ | $CH_4$ | $C_2H_6$ | $C_2H_4$ | $C_4H_8$ | CO | $CO_2$ |
| 1 | 35 | 86 | 4.2 | 3 | 0.4 | 0 | 0.7 | 6 |
| 2 | 39 | 88 | 3.2 | 2.3 | 0.3 | 0 | 0.3 | 5.4 |
| 3 | 45 | 89.6 | 2.7 | 1.9 | 0.3 | 0 | 0.3 | 4.4 |

As shown by Table 1, the regenerated catalyst showed improved propane conversion and propylene selectivity compared to the fresh catalyst. Additionally, increasing the duration of catalyst regeneration with air and steam increased propane conversion.

Example 4: Propane Dehydrogenation at 630° C.

In this Example, about 10 g of a fresh platinum catalyst was loaded into a reactor, dried, and reduced with hydrogen gas at a flow rate of 100 ml/min for thirty minutes. A feed stream containing steam and propane in a ratio of 2 mol/mol was fed to the reactor. The reaction had a temperature of 630° C., a pressure of 22 psig, and a LHSV of 1.5 $h^{-1}$.

After catalyst activity declined by 20% compared to its original activity (i.e., about 5 hours), the catalyst was regenerated with a mixture of air and steam at 550° C. for 1 hour. The flow rate of air was 75 ml/min and the flow rate of steam was 0.3215 ml/min. The catalyst was then reduced with hydrogen gas at a flow rate of 100 ml/min for thirty minutes. After regeneration, the reaction was resumed under the same conditions.

Figure 2:
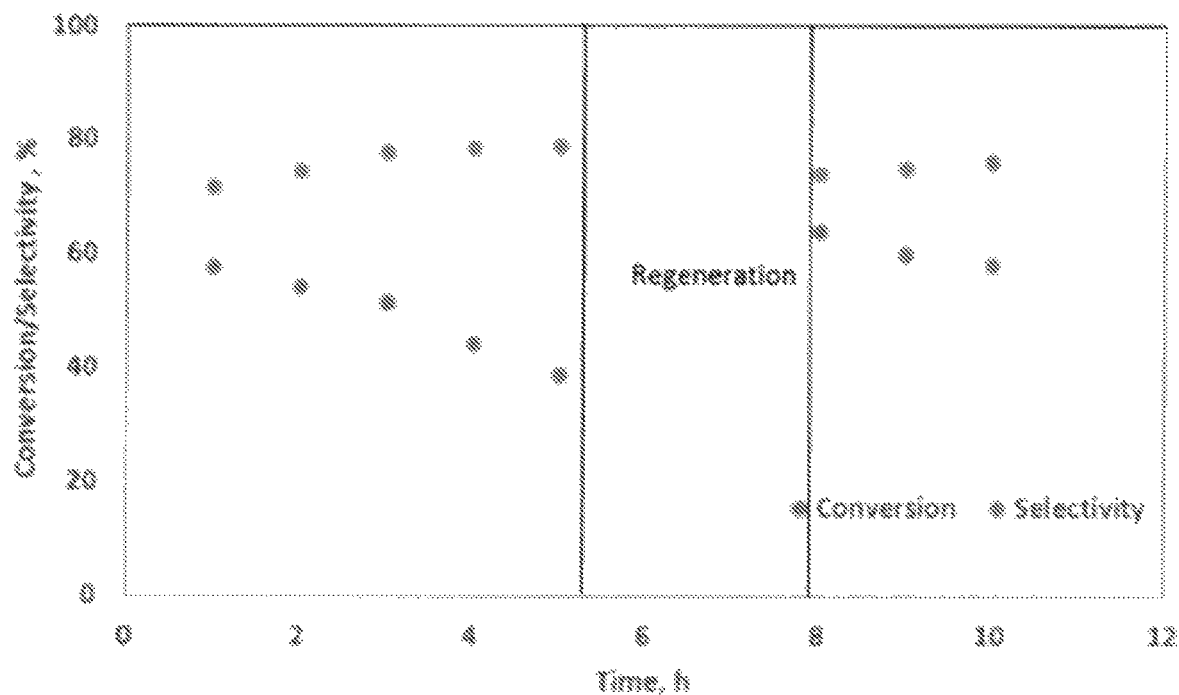
FIG. 2 illustrates propane conversion and propylene selectivity in one exemplary embodiment of methods according to the disclosed subject matter.

FIG. 2 displays propane conversion and propylene selectivity over the course of Example 4. During the first phase of the reaction, propane conversion declined from about 60% to about 40%. However, after catalyst regeneration, propane conversion was 64%. Additionally, after catalyst regeneration, propylene selectivity was 74%.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method for producing propylene and regenerating a dehydrogenation catalyst, the method comprising the steps of:
   (a) reacting a first gas mixture comprising propane in the presence of the dehydrogenation catalyst in a first reactor at a temperature of at least about 550° C. to about 630° C. to generate a product gas mixture comprising propylene;
   (b) introducing a second gas mixture comprising steam and air to the dehydrogenation catalyst at a temperature of at least about 550° C., and allowing the second gas mixture to subsist therewith for at least about one hour and up to four hours (1-4 hours); and
   (c) introducing a third gas mixture comprising hydrogen to the dehydrogenation catalyst at a temperature of at least about 500° C.;
   wherein the first reactor is selected from the group consisting of a fluidized bed reactor, a moving bed reactor and a panel reactor.

2. The method of claim 1, wherein the first gas mixture further comprises steam.

3. The method of claim 2, wherein the first gas mixture comprises steam and propane in a molar ratio from about 2 mol/mol to about 4 mol/mol.

4. The method of claim 2, further wherein the reaction temperature is 630° C.

5. The method of claim 2, wherein 50 mol-% of the propane in the first gas mixture is converted.

6. The method of claim 2, wherein 45 mol-% of the propane in the first gas mixture is converted.

7. The method of claim 2, wherein the dehydrogenation catalyst comprises platinum.

8. The method of claim 1, wherein the dehydrogenation catalyst comprises platinum.

9. The method of claim 8, wherein the platinum is supported on alumina.

10. The method of claim 1, wherein the second gas mixture is allowed to subsist with the dehydrogenation catalyst for one hour.

11. The method of claim 1, wherein the air comprises oxygen and the second gas mixture comprises from about 2 mol-% to about 10 mol-% oxygen.

12. The method of claim 1, wherein the second gas mixture comprises steam and air in a molar ratio from about 1 mol/mol to about 12 mol/mol.

13. The method of claim 1, wherein from about 35 mol-% to about 50 mol-% of the propane in the first gas mixture is converted.

14. The method of claim 1, wherein about 45 mol-% of the propane in the first gas mixture is converted.

15. The method of claim 1, wherein the reacting temperature is about 630° C.

16. The method of claim 1, wherein the reacting has a propylene selectivity of greater than about 86%.

17. The method of claim 1, wherein the first reactor is a panel reactor.

18. A method for producing propylene, the method consisting of the steps of:

introducing a first gas mixture comprising propane to a dehydrogenation catalyst at a temperature of at least about 570° C. to generate a product gas mixture comprising propylene;

introducing a second gas mixture comprising steam and air to the dehydrogenation catalyst at a temperature of at least about 550° C., and allowing the second gas mixture to subsist therewith for at least about one hour to regenerate the catalyst; and introducing a third gas mixture comprising hydrogen to the dehydrogenation catalyst at a temperature of at least about 500° C. to reduce the regenerated catalyst.

19. A method for producing propylene, the method consisting of the steps of:

(a) introducing a first gas mixture comprising propane to a dehydrogenation catalyst in a first reactor at a temperature of at least about 550° C. and up to 630° C. to generate a product gas mixture comprising propylene;

(b) introducing a second gas mixture comprising steam and air to the dehydrogenation catalyst at a temperature of at least 550° C., and allowing the second gas mixture to subsist therewith for at least about one hour; and then (c) introducing a third gas mixture comprising hydrogen to the dehydrogenation catalyst at a temperature of at least 500° C.;

wherein the first reactor is a panel reactor;

wherein the first gas mixture further comprises steam;

wherein 50 mol-% of the propane in the first gas mixture is converted;

wherein the propylene selectivity is greater than about 86%;

wherein the air comprises oxygen and the second gas mixture comprises 2 mol-% oxygen; and wherein the second gas mixture comprises steam and air in a molar ratio of 12 mol/mol.

* * * * *